United States Patent [19]

Wade et al.

[11] 4,169,148

[45] Sep. 25, 1979

[54] METHOD OF TREATING INFLAMMATORY AND PSYCHOTIC CONDITIONS WITH 1,2,4 TRIAZOLE DERIVATIVES AND COMPOSITIONS CONTAINING SAME

[75] Inventors: Peter C. Wade, Pennington, N.J.; B. Richard Vogt, Yardley, Pa.

[73] Assignee: E. R. Squibb & Sons, Inc., Princeton, N.J.

[21] Appl. No.: 939,162

[22] Filed: Sep. 1, 1978

[51] Int. Cl.$^2$ .............................................. A61K 31/41
[52] U.S. Cl. .................................................... 424/269
[58] Field of Search ......................................... 424/269

[56] References Cited

U.S. PATENT DOCUMENTS 4,006,159  2/1977  Newman ........................ 260/308 R

FOREIGN PATENT DOCUMENTS 67130    6/1969  German Democratic Rep. .
1351430  5/1974  United Kingdom .

OTHER PUBLICATIONS

Becker et al., *Journal für Praktesche* Chemie, vol. 311, (1969), pp. 477–489.

*Primary Examiner*—Stanley J. Friedman
*Attorney, Agent, or Firm*—Lawrence S. Levinson; Burton Rodney

[57] ABSTRACT

A method is provided for treating inflammatory and/or psychotic conditions with triazole derivatives, such as 3-alkyl-5-phenyl-1,2,4-triazoles. Pharmaceutical compositions containing such triazoles are also provided.

11 Claims, No Drawings

METHOD OF TREATING INFLAMMATORY AND PSYCHOTIC CONDITIONS WITH 1,2,4 TRIAZOLE DERIVATIVES AND COMPOSITIONS CONTAINING SAME

BACKGROUND OF THE INVENTION

East German Pat. No. 67,130 to Becker et al describes a procedure for the synthesis of 3,5-disubstituted-1,2,4-triazoles useful as intermediates and having the following structure

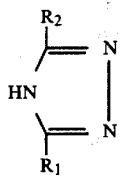

wherein $R_1$ is alkyl, aryl, aralkyl, alkoxyalkyl, acylaminoalkyl, or a heterocyclic group and $R_2$ is hydrogen, alkyl, or aryl.

Becker et al in a paper entitled "A Novel Synthesis for 3-Substituted 1,2,4-Triazoles," *Journal für praktische Chemie.* Volume 311, 1969, pages 477–489, disclose the preparation of 3-substituted-1,2,4-triazoles including 3-phenyl-1,2,4-triazoles of the structure

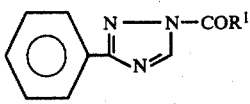

wherein $R^1$ can be ethoxy, methyl, ethyl or n-propyl. A general preparation for 1-acetyl-3-phenyl-1,2,4-triazole and 1-propionyl-3-phenyl-1,2,4-triazole is set out on page 487.

U.S. Pat. No. 4,006,159 to Newman discloses mixtures of acyl-substituted 1,2,4-triazole-3-carboxamides which may be presented by the following structural formulae:

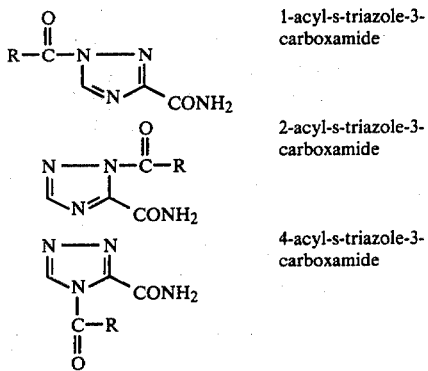

wherein each mixture consists of all three forms wherein R is the same in each form and wherein R is hydrogen, alkyl having up to 15 carbon atoms; cycloalkyl having from 3 to 8 carbon atoms; phenyl; ortho-, meta-, or para-hydroxyphenyl; ortho-, meta-, or paramethoxyphenyl; or adamantyl. The above mixtures are said to be useful as antiviral agents.

British Specification No. 1,351,430 discloses triazoles of the formula

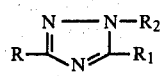

wherein R and $R_1$ are phenyl or substituted phenyl though not both simultaneously phenyl, and $R_2$ is hydrogen or $C_1$-$C_4$ alkyl, which are said to be useful as CNS depressants.

The present invention relates to a method of treating inflammatory and/or psychotic conditions with derivatives of 1,2,4-triazoles having the structure

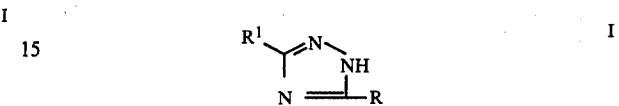

wherein R and $R^1$ may be the same or different and may be lower alkyl, cycloalkyl, cycloalkyl-lower alkyl, phenyl or phenyl-lower alkyl. Where present, the phenyl whether alone or as part of a lower alkyl group may be substituted with one or two of halogen, trifluoromethyl, lower alkyl, lower alkoxy or lower alkylthio.

In addition, the present invention relates to pharmaceutical compositions for use in treating inflammatory conditions or psychotic states, the compositions containing a triazole of formula I and a pharmaceutically acceptable carrier therefor.

The preferred compounds used in the method and composition of the invention are those of formula I wherein R and $R^1$ are each lower alkyl or phenyl or R is lower alkyl and $R^1$ is phenyl.

The term "lower alkyl" as used herein refers to alkyl groups having 1 to 7 carbons, preferably 1 to 4 carbons, including straight or branched chain groups, such as methyl, ethyl, n-propyl, i-propyl, 2-propylbutyl, n-butyl, s-butyl, i-butyl, t-butyl, n-pentyl, n-hexyl, and n-heptyl and the various branched chain isomers thereof.

The term "lower alkoxy" or "lower alkylthio" as used herein refers to lower alkyl groups as defined above attached to an oxygen atom or sulfur atom, respectively, with methoxy being preferred.

The term "cycloalkyl" as used herein refers to saturated carbocyclic radicals containing 3 to 7 carbons in the ring, such as cyclopropyl, cyclobutyl, cyclopentyl, cyclohexyl or cycloheptyl, optionally substituted with one lower alkyl group.

The term "halogen" as employed herein refers to chlorine, bromine, iodine or fluorine with chlorine and bromine being preferred.

The compounds of formula I are physiologically active substances which possess useful anti-inflammatory and central nervous system neuroleptic activities. They can be used in the treatment of rheumatoid arthritus and as major tranquilizers for mammalian species such as rats, dogs, monkeys, etc. For this purpose these compounds may be incorporated in a conventional dosage form such as tablet, capsule, injectable or the like, along with the necessary carrier material, excipient, lubricant, buffer or the like, as will be seen hereinafter, for oral or parenteral administration in single or divided doses of about 1 to 150 mg/kg/day, preferably about 5 to 75 mg/kg, two to four times daily.

The formula I compounds have antiinflammatory activity as measured by the mouse active arthus (MAA) test and/or other related tests and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis.

The neuroleptic activity of the formula I compounds is illustrated by their ability to decrease avoidance behavior in rats and monkeys according to procedures similar to that of Tenen [cf. Psychon. Sci., 6, 407-408 (1966)] as well as the ability to induce hypothermia.

The compounds of formula I may be prepared according to the procedure outlined in East German Patent 67,130 (1969), Chem. Abst. 71, 124441e or a modification thereof as described below. Thus, a nitrile of the structure

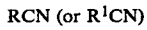    RCN (or R¹CN)    II is condensed with an amino-1,2,4-triazole of the structure

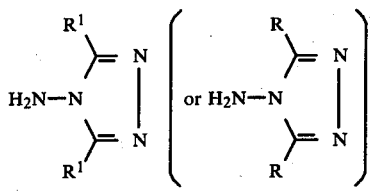

in the presence of an alkali metal hydride, such as sodium hydride or lithium hydride, and a nonreacting solvent such as dimethylformamide, dimethyl sulfoxide or dioxane, to form a compound of the structure

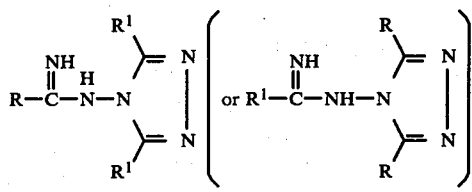

The formula IV compound is then reacted with an acid anhydride

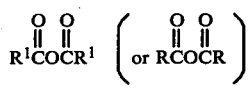    V such as acetic anhydride, propionic anhydride, butyric anhydride and the like to yield compounds of formulae VI and VII

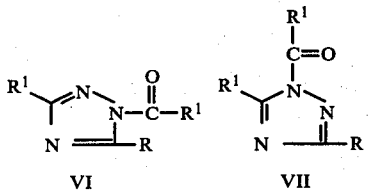

which are then easily hydrolyzed to the formula I compound.

The starting triazole of structure IV is prepared by techniques well known in the art (e.g., see Th. Curtius and G. M. Dedichen, J. Prakt, Chem., 50, 241 (1894), Beil, 26, 29). Thus, the formula IV compound may be prepared by reaction of hydrazine and an alkyl cyanide

    R¹CN    VIII under high temperatures ranging from 100° to 250°, preferably from 140° to 190° C., for periods of 0.5 to 48 hours in a sealed system, if necessary.

A compound of formula I can be administered orally or parenterally (for example, intraperitoneally, subcutaneously, intramuscularly or intravenously). Powders can be prepared by comminuting the active ingredient with a similarly comminuted diluent such as starch or lactose. Suitable forms for oral administration include capsules, tablets, troches, elixirs, wafer, chewing gum, syrups, and a suitable form for parenteral administration in a sterile injectable. Such unit dosage forms are prepared by compounding with a conventional vehicle, excipients, binders, preservatives, stabilizers, flavoring agents or the like as called for by acceptable pharmaceutical practice. Also, the compounds used in this invention can be formulated with other pharmaceutically active compounds.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples are illustrative of the invention and represent preferred embodiments. Other modifications may be readily produced by suitable variations of the reactions. All temperatures are on the Centigrade scale.

EXAMPLE 1

3-(4-Chlorophenyl)-5-methyl-1H-1,2,4-triazole

A. 4-Amino-3,5-dimethyl-4H-1,2,4-triazole

Hydrazine hydrate ($N_2H_4 \cdot H_2O$, 100 g, 2.0 mol) and acetonitrile (75 g, 1.8 mol) are weighed out into a bomb which is sealed and heated at 150° for eight hours. The reaction mixture is heated at 180° (pressure rises to 420 lb/in²) overnight. After the bomb is cooled, vented and opened, a white solid plus some liquid remains. The solid is collected on a filter washed with a small amount of cold water, toluene, and recrystallized from 600 ml of ethyl acetate to give 51 g of the title A compound, m.p. 195°-197° C.

B.
4-Chloro-N-(3,5-dimethyl-4H-1,2,4-triazol-4-yl)benzenecarboximidamide 15.32 g (364 mM) Sodium hydride (57% oil dispersion) is washed with ether (X 5) in a sintered glass funnel to remove the oil. The free sodium hydride is washed with a little DMSO into a stirred suspension of 50.0 g (363 mM) of 4-chlorobenzonitrile and 40.7 g (363 mM) of 4-amino-3,5-dimethyl-4H-1,2,4-triazole (prepared in part A) in 200 ml of DMSO (distilled from CaH$_2$ under vacuum). After the addition, the mixture is stirred in an ice bath for 1 hour and for 3 hours at room temperature. The reaction mixture is poured into 2 liters of ice water and stirred for 15 minutes until the floculant precipitate coagulates into a filterable state. The product is then filtered out, washed with water, and dried at 50° under vacuum overnight to yield 94.2 g of the title B compound, m.p. 303°–306°. (This material is suitable for use in part C.)

C.
1-Acetyl-3-(4-chlorophenyl)-5-methyl-1H-1,2,4-triazole 63.6 g (254.0 mM) 4-Chloro-N-(3,5-dimethyl-4H-1,2,4-triazol-4-yl)benzenecarboximidamide prepared in part B and 67 ml of acetic anhydride in a 300 ml round bottom flask equipped with a distillation head are heated to 170° in an oil bath. A solution forms from which acetic acid distills off in the first few minutes. The mixture is refluxed for 2.5 hours and the excess acetic anhydride is evaporated to dryness under vacuum to produce a residue comprising a mixture of the title compound and its 1-acetyl-5-(4-chlorophenyl)-3-methyl isomer. The residue is triturated with 120 ml of water at room temperature and filtered. The filter cake is dissolved in 1 liter of hot ethanol, filtered hot, and the product precipitated from the hot alcohol by adding 3 liters of cold water. The product is filtered off, washed with water, and dried at 80° under vacuum to yield 37.6 g of the 1-acetyl-3-(4-chlorophenyl)-5-methyl-1H-1,2,4-triazole as a crystalline material (99% pure), m.p. 132°–133°.

D. 3-(4-Chlorophenyl)-5-methyl-1H-1,2,4-triazole 27 g (114 mM) 1-Acetyl-3-(4-chlorophenyl)-5-methyl-1H-1,2,4-triazole is refluxed in 800 ml of water for 9 hours and stirred overnight at room temperature. The product is filtered out, washed with water, and dried at 90° under vacuum overnight to give 23.4 g of the title compound, m.p. 173°–175°.

EXAMPLES 2 TO 16

Following the procedure of Example 1, but substituting for 4-chloro benzonitrile, the compound shown in Column I of Table A below, substituting for the aminotriazole, the compound shown in Column II, the compound used in the method and compositions of the invention and shown in Column III is obtained.

TABLE A

| Ex. No. | Column I RCN — R | Column II (H$_2$N—N structure) R$^1$ | Column III R | R$^1$ |
|---|---|---|---|---|
| 2. | phenyl (S) | phenyl (S) | As in Column I | As in Column II |
| 3. | CH$_3$ | CH$_3$ | | |
| 4. | C$_6$H$_4$CH$_2$— | C$_2$H$_5$ | | |
| 5. | CH$_3$ | CH$_3$—(cyclopropyl S) | | |
| 6. | p-CH$_3$O—C$_6$H$_4$ | C$_2$H$_5$ | | |
| 7. | C$_6$H$_5$ | C$_6$H$_5$ | | |
| 8. | p-Cl—C$_6$H$_4$ | CH$_3$ | | |
| 9. | p-CF$_3$—C$_6$H$_4$— | (cyclopropyl S) | | |
| 10. | 3,5-dichloro-4-hydroxyphenyl (Cl—O—Cl) | C$_6$H$_5$ | | |
| 11. | C$_6$H$_5$ | C$_2$H$_5$ | | |
| 12. | m-C$_2$H$_5$OC$_6$H$_4$ | n-C$_4$H$_9$ | | |
| 13. | p-C$_2$H$_5$—C$_6$H$_4$ | p-C$_2$H$_5$—C$_6$H$_4$ | | |
| 14. | (cyclopropyl S)—CH$_2$— | (cyclopropyl S)—CH$_2$— | | |
| 15. | C$_6$H$_5$ | phenyl—(CH$_2$)$_2$— | | |
| 16. | p-CH$_3$S—C$_6$H$_4$— | (cyclopropyl S) | | |

EXAMPLE 17

Parenteral Composition Containing 3-(4-Chlorophenyl)-5-methyl-1H-1,2,4-triazole A dispersion suitable for parenteral administration is prepared by dispersing 1 mg of 3-(4-chlorophenyl)-5-methyl-1H-1,2,4-triazole in about 100 ml of water for injection.

EXAMPLE 18

Tablets Containing 3-(4-Chlorophenyl)-5-methyl-1H-1,2,4-triazole

The following ingredients are used to make 1,000 200 mg tablets each containing 100 mg of active ingredient:

| | |
|---|---|
| 3-(4-Chlorophenyl)-5-methyl-1H-1,2,4-triazole | 100 gm |
| Polyvinyl pyrrolidone | 7.5 gm |
| Lactose | 20 gm |
| Magnesium stearate | 3.5 gm |
| Corn starch | 17.5 gm |
| Avicel (microcrystalline cellulose) | 51.5 gm |

The medicament and lactose are thoroughly admixed, the polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg tablets on a standard concave punch. The tablets are then veneer coated with methyl cellulose in a spray gun.

The formulations of Examples 17 and 18 as well as similar formulations containing the compounds of Examples 2 to 16 may be employed in treating inflammatory conditions and/or psychotic conditions in mammals.

What is claimed is:

1. A method for treating an inflammatory condition in a mammalian host requiring such treatment, which comprises administering to a mammalian host requiring such treatment an effective amount of a composition comprising a compound of the structure

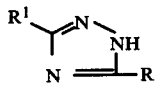

wherein R and R$^1$ may be the same or different and may be lower alkyl, cycloalkyl, cycloalkyl-lower alkyl, phenyl or phenyl-lower alkyl, said phenyl whether present as an independent group or as a substituent on said lower alkyl group being optionally substituted with one or two substituents selected from the group consisting of halogen, trifluoromethyl, lower alkyl, lower alkoxy, or lower alkylthio, and a physiologically acceptable carrier therefor.

2. The method as defined in claim 1 where in said compound R and R$^1$ are each lower alkyl.

3. The method as defined in claim 1 where in said compound R and R$^1$ are each phenyl.

4. The method as defined in claim 1 where in said compound R is lower alkyl and R$^1$ is phenyl.

5. The method as defined in claim 1 where in said compound R is halophenyl and R$^1$ is lower alkyl.

6. The method as defined in claim 1 wherein said composition includes 3-(4-chlorophenyl)-5-methyl-1H-1,2,4-triazole as the active component.

7. A method for treating psychotic states in a mammalian host requiring such treatment, which comprises administering to a mammalian host requiring such treatment an effective amount of the composition comprising a compound of the structure

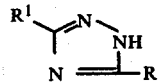

wherein R and R$^1$ may be the same or different and may be lower alkyl, cycloalkyl, cycloalkyl-lower alkyl, phenyl or phenyl-lower alkyl, said phenyl whether present as an independent group or as a substituent on said lower alkyl group being optionally substituted with one or two substituents selected from the group consisting of halogen, trifluoromethyl, lower alkyl, lower alkoxy, or lower alkylthio, and a physiolgically acceptable carrier therefor.

8. The method as defined in claim 7 where in said compound R and R$^1$ are each lower alkyl.

9. The method as defined in claim 7 where in said compound R is lower alkyl and R$^1$ is phenyl.

10. The method as defined in claim 7 where in said compound R is halophenyl and R$^1$ is lower alkyl.

11. The method as defined in claim 7 wherein said composition includes 3-(4-chlorophenyl)-5-methyl-1H-1,2,4-triazole as the active compound.

* * * * *